United States Patent
Kang et al.

(10) Patent No.: US 8,218,136 B2
(45) Date of Patent: Jul. 10, 2012

(54) APPARATUS AND METHOD FOR RECOGNIZING HOME POSITION OF ROTATABLE BODY

(75) Inventors: Kyu-tae Kang, Suwon-si (KR); Jong-gun Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 391 days.

(21) Appl. No.: 12/512,513

(22) Filed: Jul. 30, 2009

(65) Prior Publication Data

US 2010/0177325 A1   Jul. 15, 2010

(30) Foreign Application Priority Data

Jan. 15, 2009   (KR) .................. 10-2009-0003406

(51) Int. Cl.
 *G01B 11/26* (2006.01)
(52) U.S. Cl. ....................................... 356/153
(58) Field of Classification Search ............. None
 See application file for complete search history.

(56) References Cited

U.S. PATENT DOCUMENTS

| | | | | |
|---|---|---|---|---|
| 4,843,388 A | * | 6/1989 | Miyamoto | ............ 341/15 |
| 4,868,385 A | * | 9/1989 | Nishimura | ......... 250/231.16 |
| 7,110,593 B2 | * | 9/2006 | Katagiri et al. | ............ 382/154 |

FOREIGN PATENT DOCUMENTS

| | | |
|---|---|---|
| EP | 1775589 A1 | 4/2007 |
| EP | 1775592 A1 | 4/2007 |
| EP | 1983347 A2 | 10/2008 |
| JP | 1994-003163 A | 1/1994 |
| JP | 1995-170696 A | 7/1995 |
| JP | 1997-280894 A | 10/1997 |
| JP | 1997-280895 A | 10/1997 |
| JP | 2003-336711 A | 11/2003 |
| JP | 2006-286131 A | 10/2006 |
| WO | 2006/024109 A1 | 3/2006 |

* cited by examiner

*Primary Examiner* — Tu Nguyen
(74) *Attorney, Agent, or Firm* — Sughrue Mion, PLLC

(57) ABSTRACT

Provided are an apparatus and method for recognizing a home position of a rotatable body. The apparatus includes: a tray including a support surface on which the rotatable body can be seated; a rotatable body position alignment unit for controlling the position of the rotatable body so that the rotatable body is aligned to be in a predetermined position when the rotatable body is seated on the support surface of the tray; a motor including a motor shaft that rotates by power supply, and a turntable that can be coupled with the rotatable body and rotates the rotatable body; and an encoder that is connected to the motor shaft and generates signals for measuring a rotational angle and a rotational direction of the motor shaft.

18 Claims, 5 Drawing Sheets

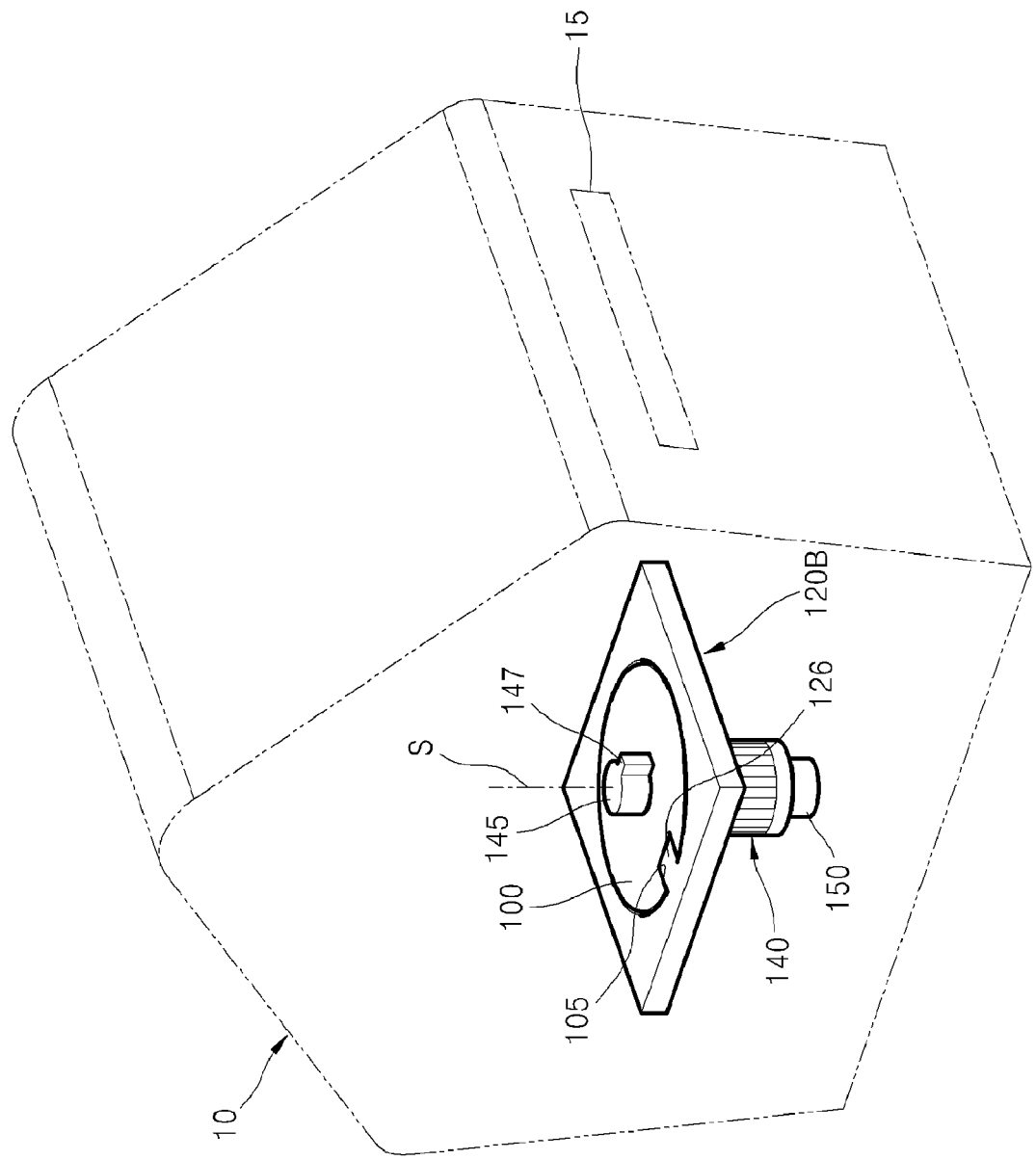

APPARATUS AND METHOD FOR RECOGNIZING HOME POSITION OF ROTATABLE BODY

CROSS-REFERENCE TO RELATED APPLICATION

This application claims priority from Korean Patent Application No. 10-2009-0003406, filed on Jan. 15, 2009, in the Korean Intellectual Property Office, the disclosure of which is incorporated herein in its entirety by reference.

BACKGROUND

1. Field

One or more embodiments relate to an apparatus and method for recognizing a home position of a rotatable body such as a disc-shaped microfluidic apparatus.

2. Description of the Related Art

In microfluidics, research into disc-shaped microfluidic apparatuses that are used to perform immunoserology and gene tests for a short time period is being conducted. Disc-shaped microfluidic apparatuses are referred to as a Lab Compact Disc (CD) or a Lab-on-a-CD, and transport a fluid by using a centrifugal force generated due to their rotary motion.

In order to perform biological sample reactions and detect reaction results in such a microfluidic apparatus, the positions of structures placed in microfluidic apparatus, such as valves, functional units, or chambers for sensing reactions, need to be precisely recognized. In the related art, a process of recognizing a home position, which is a reference position to identify the positions of structures, is performed and then, the positions of the structures are identified. The home position can be recognized by using a light source for irradiating light, a mark that is formed in the rotatable body and reflects light irradiated from the light source, and an optic sensor that senses the reflected light.

SUMMARY

One or more embodiments include an apparatus and method for recognizing a home position of a rotatable body, without a process or sensor for recognizing the home position of the rotatable body.

Additional aspects will be set forth in part in the description which follows and, in part, will be apparent from the description, or may be learned by practice of the invention.

To achieve the above and/or other aspects, one or more embodiments may include an apparatus for recognizing a home position of a rotatable body, the apparatus including: the rotatable body; a tray including a support surface on which the rotatable body can be seated; a rotatable body position alignment unit for controlling the home position of the rotatable body in such a way that only when the rotatable body is aligned to be in a predetermined position, the rotatable body is seated on the support surface of the tray; a motor including a motor shaft that rotates by power supply and a turntable that can be coupled with the rotatable body and rotates the rotatable body; and an encoder that is connected to the motor shaft and generates signals for measuring a rotational angle and rotational direction of the motor shaft, wherein when the encoder outputs a Z-phase signal, the turntable is coupled with the rotatable body so that the rotatable body rotates, or the turntable is separated from the rotatable body so that rotary motion of the rotatable body stops and the rotatable body is seated on the support surface of the tray.

The rotatable body position alignment unit includes: a protrusion that is formed in the tray and protrudes toward the rotatable body; and a groove that is formed in the rotatable body and is recessed corresponding to the protrusion.

The apparatus may further include an elasticity application unit that elastically presses against the rotatable body to reduce a positioning error of the rotatable body and is formed in the protrusion or the turntable.

The rotatable body may have an engagement hole in a central portion of the rotatable body so that the turntable can be inserted into and coupled with the rotatable body, the support surface of the tray may have an opening through which the turntable is passable, and the turntable is lifted through the opening of the support surface of the tray and is coupled with the engagement hole of the rotatable body and is descended through the opening of the support surface of the tray and is separated from the engagement hole of the rotatable body.

The turntable may lift the rotatable body seated on the support surface of the tray so that the turntable is separated from the support surface of the tray, and after the rotatable body is seated on the support surface of the tray, the turntable is descended further from the rotatable body so that the turntable is separated from the rotatable body.

The rotatable body may be a microfluidic apparatus for performing a biochemical reaction using a small amount of a biological sample.

The tray may be slideable between a first position in which a lengthwise direction extension line of the motor shaft passes through a central portion of the rotatable body seated on the support surface of the tray and a second position in which the tray is located out of the lengthwise direction extension line of the motor shaft.

To achieve the above and/or other aspects, one or more embodiments may include a method of recognizing a home position of a rotatable body, the method including: mounting the rotatable body, the mounting including aligning the rotatable body to be in a predetermined position and seating the aligned rotatable body on a support surface of a tray; and coupling a turntable with the rotatable body when an encoder that is connected to a motor shaft for rotating the rotatable body outputs a Z-phase signal.

The method may further include: driving the rotatable body, the driving including separating the rotatable body from the support surface of the tray and rotating the turntable and the rotatable body coupled with the turntable; stopping the rotary motion of the rotatable body when the encoder outputs the Z-phase signal, so that the rotatable body is aligned to be in a predetermined position; and separating the turntable from the rotatable body, the separating including seating the rotatable body on the support surface of the tray and separating the turntable from the rotatable body.

BRIEF DESCRIPTION OF THE DRAWINGS

These and/or other aspects will become apparent and more readily appreciated from the following description of the embodiments, taken in conjunction with the accompanying drawings, in which:

FIGS. 2A through 2C are perspective views for sequentially explaining a method of recognizing a home position of a rotatable body by using an apparatus for recognizing the home position, according to another embodiment.

DETAILED DESCRIPTION

Figure 1:
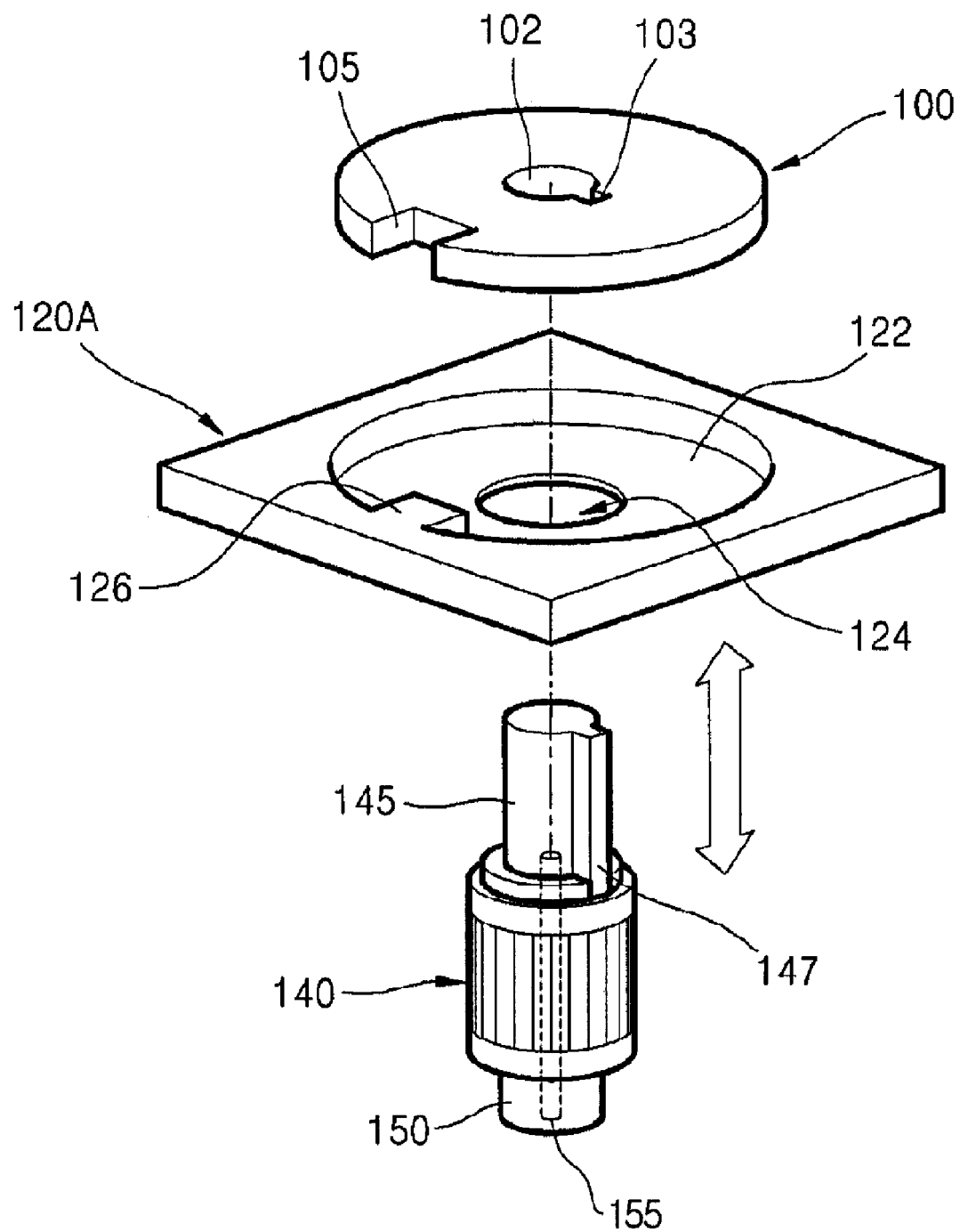
FIG. 1 is a perspective view of an apparatus for recognizing a home position of a rotatable body according to an embodiment.

Reference will now be made in detail to embodiments, examples of which are illustrated in the accompanying drawings, wherein like reference numerals refer to like elements throughout. In this regard, the embodiments may have different forms and should not be construed as being limited to the descriptions set forth herein. Accordingly, the embodiments are merely described below, by referring to the drawings, to explain aspects of the present description.

Hereinafter, an apparatus and method for recognizing a home position of a rotatable body according to one or more embodiments will be described in detail with reference to the attached drawings.

FIG. 1 is a perspective view of an apparatus for recognizing a home position of a rotatable body 100 according to an embodiment.

Referring to FIG. 1, the apparatus may include the rotatable body 100. The rotatable body 100 may be a disc-shaped microfluidic apparatus. The apparatus may also include: a tray 120A having a support surface 122 on which the rotatable body 100 can be seated; a motor 140 including a motor shaft 155 that rotates by power supply, and a turntable 145 that can be coupled with the rotatable body 100 and rotate the rotatable body 100; and an encoder 150 that is connected to the motor shaft 155 and generates signals for measuring a rotational angle and a rotational direction of the motor shaft 155.

The disc-shaped microfluidic apparatus is used to perform a biochemical reaction using a small amount of a biological sample. Although not illustrated in FIG. 1, the disc-shaped microfluidic apparatus may include chambers for accommodating a fluid, channels through which the fluid flows, valves for adjusting the fluid flow, or various functional units for performing a predetermined function using the fluid. The rotatable body 100 may have an engagement hole 102 in a central portion of the rotatable body 100 to allow the turntable 145 to be inserted into the rotatable body 100. The turntable 145 has an alignment protrusion 147 that protrudes in a radial direction of the turntable 145, and the engagement hole 102 of the rotatable body 100 has an alignment groove 103 corresponding to the alignment protrusion 147. If the turntable 145 and the engagement hole 102 are aligned with one another and the turntable 145 is inserted into the engagement hole 102 in such a way that the alignment protrusion 147 is correspondingly inserted in the alignment groove 103, when the turntable 145 rotates, the rotatable body 100 is synchronized with the turntable 145 and rotates together with the turntable 145. In this case, idling rotation of the rotatable body 100 with respect to the turntable 145 is prevented.

The support surface 122 of the tray 120A has an opening 124 through which the turntable 145 is passable. The turntable 145 can be upwardly inserted through the opening 124 of the support surface 122 and is coupled with the engagement hole 102 of the rotatable body 100. Also, the turntable 145 can be downwardly lowered through the opening 124 and is separated from the engagement hole 102 of the rotatable body 100.

The apparatus may further include a rotatable body position alignment unit that controls the position of the rotatable body 100 in such a way that only when the rotatable body 100 is aligned to be in a predetermined position, the rotatable body 100 is seated on the support surface 122 of the tray 120A. The rotatable body position alignment unit may include a protrusion 126 that is formed in the tray 120A and protrudes toward the rotatable body 100 so that the protrusion can correspond to a groove 105 that is formed in the rotatable body 100 and is recessed to correspond to the protrusion 126. Due to the protrusion 126, only when the groove 105 is positioned to correspondingly receive the protrusion 126, the rotatable body 100 is seated on the support surface 122.

The encoder 150 outputs A-phase, B-phase, and Z-phase signals as the motor shaft 155 rotates. The Z-phase signal is regularly generated once whenever the motor shaft 155 makes one complete rotation. In the rotatable body position alignment unit, when the rotatable body 100 is seated on the support surface 122 and the turntable 145 is aligned so as to be inserted into the engagement hole 102 of the rotatable body 100, in other words, when the alignment groove 103 of the engagement hole 102 and the alignment protrusion 147 of the turntable 145 are aligned, the encoder 150 is initialized to output the Z-phase signal.

In a case in which the rotatable body 100 is seated on the support surface 122, when the encoder 150 outputs the Z-phase signal while the turntable 145 fixed to the motor shaft 155 rotates, the turntable 145 stops. Then, the turntable 145 is upwardly inserted into the engagement hole 102, thereby coupling with the rotatable body 100 (see FIG. 2B.) Then, if the turntable 145 is lifted further, the rotatable body 100 is lifted together with the turntable 145, and separates from the support surface 122 (see FIG. 2C.) Then, the rotatable body 100 is rotated by rotating the turntable 145. A position of the rotatable body 100 when the rotatable body 100 begins to rotate is maintained uniform due to the protrusion 126, and the rotational angle may be precisely determined according to an output signal of the encoder 150. Accordingly, despite the rotary motion of the rotatable body 100, the location of chambers, channels, valves, or functional units, which are included in the rotatable body 100, may be precisely identified.

To seat the rotatable body 100 back on the tray 120A, when the encoder 150 outputs the Z-phase signal, the rotary motion is stopped. In this case, the protrusion 126 of the tray 120A and the groove 105 of the rotatable body 100 are aligned. Then, the turntable 145 is descended so that the rotatable body 100 is seated on the support surface 122. Then, the turntable 145 is descended further from the tray 120A, thereby separating the turntable 145 from the rotatable body 100.

Figure 2A:
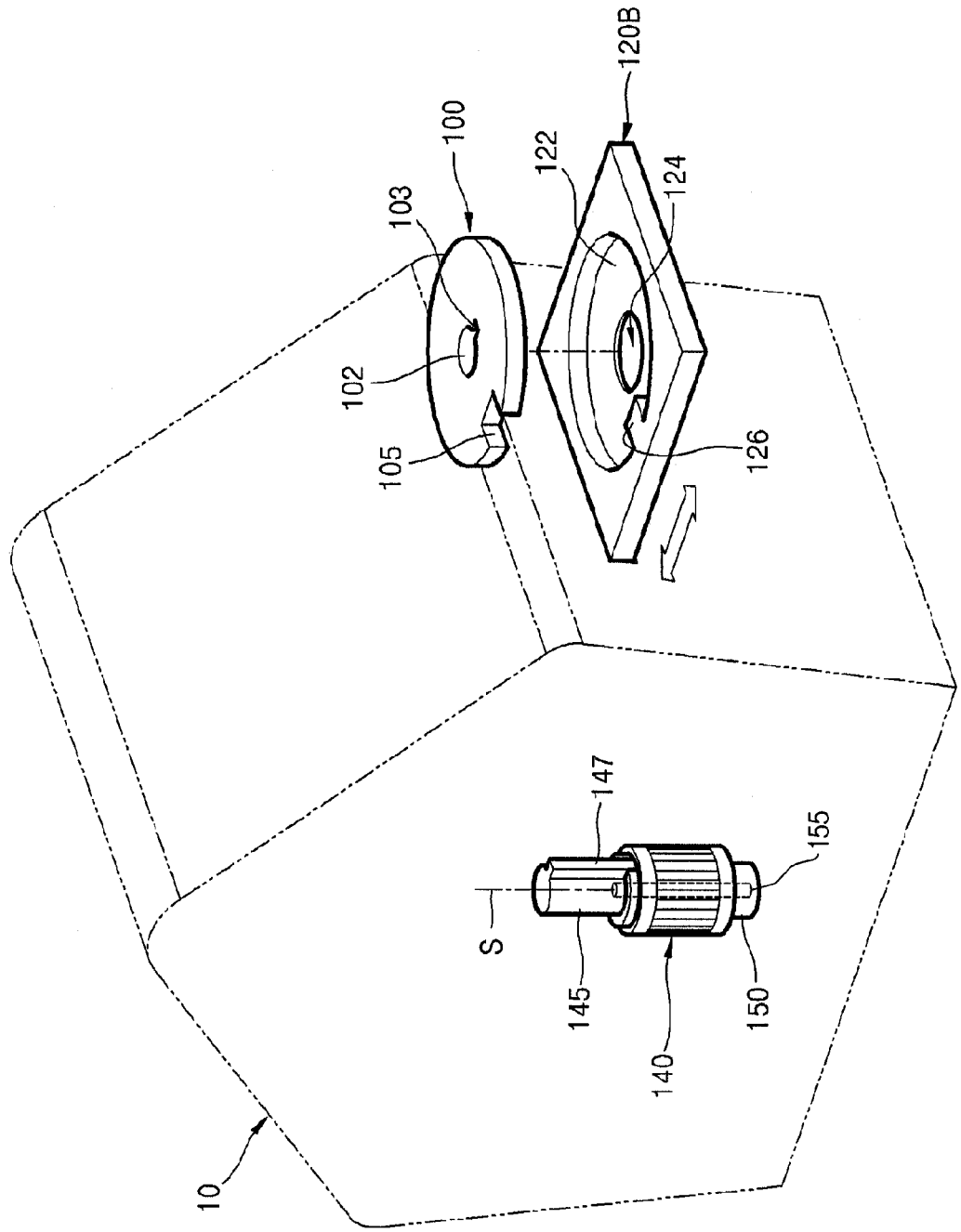
Figure 2C:
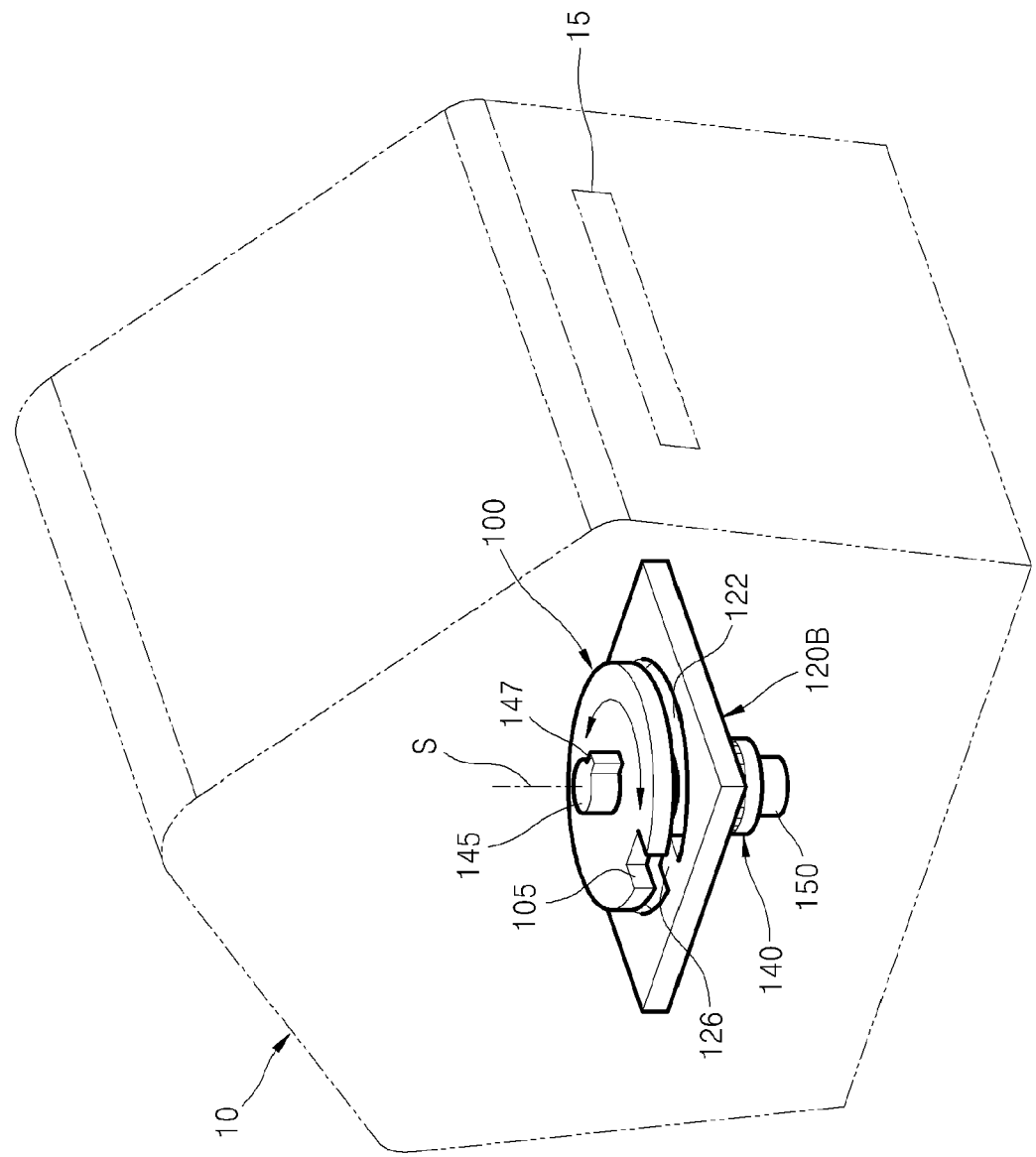

FIGS. 2A through 2C are perspective views for sequentially explaining a method of recognizing a home position of a rotatable body by using an apparatus for recognizing the home position of the rotatable body, according to another embodiment. Hereinafter, the apparatus for recognizing a home position of a rotatable body and the method of recognizing a home position of the rotatable body will be described in detail with reference to FIGS. 2A through 2C. Like elements illustrated in FIGS. 1 and 2A through 2C are denoted by like reference numerals. Accordingly, the method and apparatus for recognizing the home position of the rotatable body 100 of FIGS. 2A through 2C will now be described in terms of differences between the method and apparatus for recognizing the home position of the previous embodiment that is shown in FIG. 1 and the method and apparatus for recognizing the home position that is shown in FIGS. 2A through 2C.

Referring to FIG. 2A, the apparatus for recognizing a home position of the rotatable body 100 may be included in a biochemical analyzer 10. The biochemical analyzer 10 may provide outer conditions appropriate for a biological sample reaction that is measurable in the rotatable body 100 such as a microfluidic apparatus, and detects the results of the biological sample reaction that occurs in the microfluidic apparatus 100. The apparatus includes the rotatable body 100, a tray 120B having the support surface 122 on which the rotatable body 100 can be seated, the motor 140 including the motor shaft 155 and the turntable 145, and the encoder 150 that is connected to the motor shaft 155. Since the rotatable body 100, the motor 140, and the encoder 150 have already been described with reference to FIG. 1, the rotatable body 100, the motor 140, and the encoder 150 will not be described in detail in this section.

The tray 120B has the support surface 122 on which the rotatable body 100 can be seated, and the support surface 122 has the opening 124 through which the turntable 145 is passable. In the biochemical analyzer 10, the tray 120B is slideable between a first position (see FIGS. 2B and 2C) in which a lengthwise direction extension line S of the motor shaft 155 passes through a central portion of the rotatable body 100 seated on the support surface 122 and a second position (see FIG. 2A) in which the tray 120B is located out of the lengthwise direction extension line S of the motor shaft 155. The tray 120B is moved from the first position to the second position through a slot (see 15 of FIG. 2B) of the biochemical analyzer 10.

The method of recognizing a home position of the rotatable body 100 by using the apparatus described above may include: mounting the rotatable body 100, the mounting including aligning the rotatable body 100 to be in a predetermined position and seating the aligned rotatable body 100 on the support surface 122 of the tray 120B; and coupling the turntable 145 with the rotatable body 100 when the encoder 150 outputs the Z-phase signal. In addition, the method of recognizing a home position of the rotatable body 100 may further include: driving the rotatable body 100, the driving including separating the rotatable body 100 from the support surface 122 and rotating the turntable 145 and the rotatable body 100 coupled with the turntable 145; stopping the rotary motion of the rotatable body 100 when the encoder 150 outputs the Z-phase signal, so that the rotatable body 100 is aligned to be in a predetermined position; and separating the turntable 145 from the rotatable body 100, the separating including seating the rotatable body 100 on the support surface 122 and separating the turntable 145 from the rotatable body 100.

Specifically, to mount the rotatable body 100, the tray 120B is moved to the second position, the groove 105 of the rotatable body 100 is aligned with the protrusion 126 of the tray 120B, and the rotatable body 100 is descended onto the support surface 122 of the tray 120B, thereby seating the rotatable body 100 on the support surface 122 of the tray 120B.

Referring to FIG. 2B, the coupling of the turntable 145 with the rotatable body 100 may include moving the tray 120B to the first position, rotating the turntable 145 of the motor 140 until the encoder 150 outputs the Z-phase signal, and when the Z-phase signal is generated, stopping the rotary motion of the turntable 145 and lifting the turntable 145. The lifted turntable 145 is correspondingly inserted into the engagement hole 102 of the rotatable body 100 and coupled with the rotatable body 100.

Referring to FIG. 2C, the driving of the rotatable body 100 may include separating the rotatable body 100 from the support surface 122 by further lifting the turntable 145 when the rotatable body 100 is seated on the support surface 122, and, in this separation state, rotating the rotatable body 100 by rotating the turntable 145. When the rotatable body 100 begins to rotate, the position of the rotatable body 100 is maintained uniform due to the protrusion 126, and the rotational angle is precisely identified by referring to an output signal of the encoder 150. Accordingly, despite the rotary motion of the rotatable body 100, the location of chambers, channels, valves, or functional units, which are included in the rotatable body 100, may be precisely identified.

The stopping of the rotary motion of the rotatable body 100 includes stopping the rotary motion of the turntable 145 when the encoder 150 outputs the Z-phase signal. When the rotary motion of the rotatable body 100 is stopped, the protrusion 126 of the tray 120B and the groove 105 of the rotatable body 100 are aligned. The separating of the turntable 145 from the rotatable body 100 includes seating the rotatable body 100 on the support surface 122 by lowering the turntable 145 and separating the turntable 145 from the rotatable body 100 by lowering the turntable 145 further from the tray 120B. Then, the tray 120B is moved to the second position illustrated in FIG. 2A and the rotatable body 100 is removed from the biochemical analyzer 10.

Figure 3:
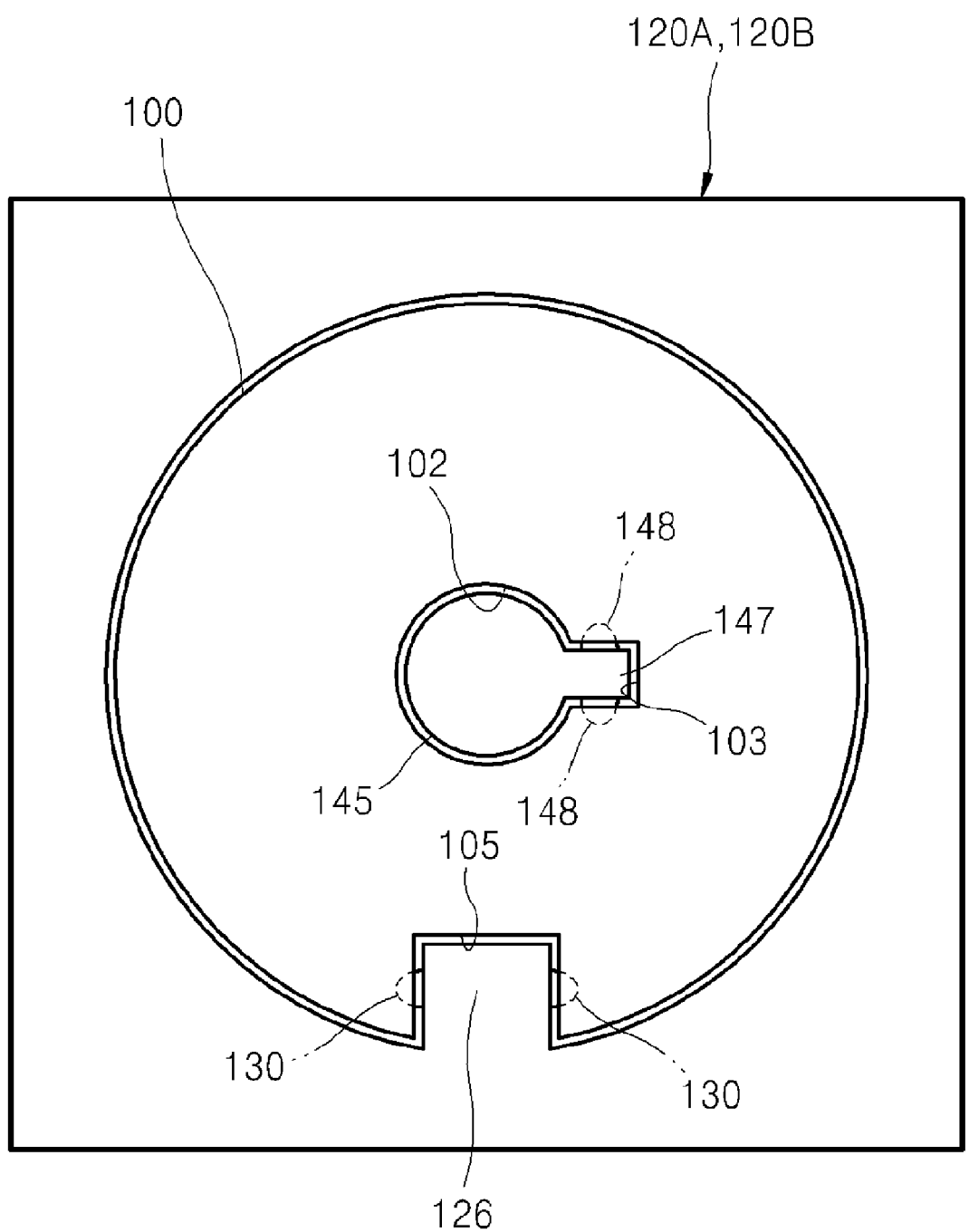
FIG. 3 is a plan view of the apparatus illustrated in FIG. 1 or FIGS. 2A through 2C, wherein the rotatable body is seated on a tray and inserted into a turntable, according to an embodiment.

FIG. 3 is a plan view of the apparatus illustrated in FIG. 1 or FIGS. 2A through 2C, wherein the rotatable body 100 is seated on the tray 120A or 120B and inserted into the turntable 145, according to an embodiment.

Referring to FIG. 3, the apparatus may further include an elasticity application unit that elastically presses against the rotatable body 100 to reduce a positioning error of the rotatable body 100. For example, the elasticity application unit may include a first ball plunger 130 that elastically presses against an inner surface of the groove 105 of the rotatable body 100 and is formed in the protrusion 126 of the tray 120A or 120B, or a second ball plunger 148 that elastically presses against an inner surface of the alignment groove 103 of the rotatable body 100 and is formed in the alignment protrusion 147 of the turntable 145. To further reduce the positioning error of the rotatable body 100, the inner surface of the groove 105 and the inner surface of the alignment groove 103 which are elastically pressed by the ball plungers 130 and 148 may be partly recessed to form grooves having an appropriate size to receive the ball plungers 130 and 148.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An apparatus for determining a home position of a rotatable body, the apparatus comprising:

a tray comprising a support surface on which the rotatable body can be seated;

a rotatable body position alignment unit that controls the home position of the rotatable body so that the rotatable body is aligned to be in a predetermined position at the rotatable body position alignment unit when the rotatable body is seated on the support surface of the tray;

a motor comprising a motor shaft that rotates and a turntable that is configured to be coupled with the rotatable body to rotate the rotatable body; and an encoder that is connected to the motor shaft and outputs signals for measuring a rotational angle and a rotational direction of the motor shaft, wherein, in accordance with at least one of the output signals, the turntable is coupled with or separated from the rotatable body.

2. The apparatus of claim 1, wherein the output signals comprise a Z-phase signal, and wherein when the encoder outputs the Z-phase signal, the turntable is coupled with the rotatable body so that the rotatable body rotates, or the turntable is separated from the rotatable body so that a rotary motion of the rotatable body stops and the rotatable body is seated on the support surface of the tray.

3. The apparatus of claim 1, wherein the home position of the rotatable body is determined with respect to at least one of a rotational angle and a rotational direction of the motor shaft.

4. The apparatus of claim 1, wherein the rotatable body position alignment unit comprises a protrusion that is formed in the tray and corresponds to a groove that is formed in the rotatable body.

5. The apparatus of claim 4, further comprising an elasticity application unit that elastically presses against the rotatable body to reduce a positioning error of the rotatable body and is formed in at least one of the protrusion and the turntable.

6. The apparatus of claim 1, wherein the rotatable body comprises an engagement hole in a central portion of the rotatable body so that the turntable can be inserted into and coupled with the rotatable body,
wherein the support surface of the tray comprises an opening through which the turntable is lifted to be coupled with the engagement hole of the rotatable body, and is lowered to be separated from the engagement hole of the rotatable body.

7. The apparatus of claim 1, wherein the turntable lifts the rotatable body seated on the support surface of the tray so that the rotatable body is separated from the support surface of the tray, and
wherein after the rotatable body is seated on the support surface of the tray, the turntable is lowered further from the rotatable body so that the turntable is separated from the rotatable body.

8. The apparatus of claim 1, wherein the rotatable body is an apparatus for performing a biochemical reaction with a biological sample.

9. The apparatus of claim 1, wherein the tray is slideable between a first position in which a lengthwise direction extension line of the motor shaft passes through a central portion of the rotatable body seated on the support surface of the tray, and a second position in which the tray is located out of the lengthwise direction extension line of the motor shaft.

10. The apparatus of claim 1, wherein the encoder outputs a signal comprising a Z-phase signal when the rotatable body is aligned to be in the home position and the turntable is aligned so as to be coupled with the rotatable body.

11. The apparatus of claim 10, wherein the turntable lifts the rotatable body seated on the support surface of the tray so that the turntable is separated from the support surface of the tray and the turntable rotates, and
wherein the rotatable body stops rotating when the encoder outputs the signal and the turntable is lowered with the rotatable body so that the rotatable body sits on the support surface of the tray.

12. A method of recognizing a home position of a rotatable body, the method comprising:
mounting the rotatable body by aligning the rotatable body to be in a predetermined position and seating the aligned rotatable body on a support surface of a tray; and
coupling a turntable with the rotatable body when an encoder that is connected to a motor shaft for rotating the rotatable body outputs a Z-phase signal.

13. The method of claim 12, further comprising:
driving the rotatable body, the driving comprising separating the rotatable body from the support surface of the tray and rotating the turntable and the rotatable body coupled with the turntable;
stopping the rotary motion of the rotatable body when the encoder outputs the Z-phase signal, so that the rotatable body is aligned to be in the predetermined position; and
separating the turntable from the rotatable body, the separating comprising seating the rotatable body on the support surface of the tray and separating the turntable from the rotatable body.

14. The method of claim 13, wherein the driving further comprises determining at least one of a rotational angle and a rotational direction of the motor shaft using an output signal output from the encoder.

15. An apparatus for determining a home position of a rotatable body, the apparatus comprising:
a tray on which the rotatable body can be seated, the tray comprising an alignment unit that controls the home position of the rotatable body by
aligning the rotatable body to the alignment unit when the rotatable body is seated on the tray;
a motor comprising a motor shaft that rotates and a turntable that is configured to be coupled with the rotatable body to rotate the rotatable body; and
an encoder that is connected to the motor shaft and outputs signals for measuring at least one of a rotational angle and a rotational direction of the motor shaft, thereby determining the home position of the rotatable body.

16. The apparatus of claim 15, wherein the tray has a support portion, recessed from an upper surface, on which the rotatable body is seated, and
wherein the alignment unit comprises a protrusion protruded from an outer circumference surface of the support portion to engage a groove formed on the rotatable body.

17. The apparatus of claim 16, wherein the turntable comprises an alignment protrusion to be coupled with the rotatable body.

18. The apparatus of claim 15, wherein the tray comprises an opening through which the turntable passes from below to be coupled with the rotatable body, and
wherein the rotational angle is determined with respect to the alignment unit according to at least one of the signals output by the encoder when the rotatable body, coupled with the turntable, is lifted and separated from the tray, and is rotated by the turntable, thereby determining the home position of the rotatable body.

* * * * *